(12) United States Patent
Turovets

(10) Patent No.: US 11,020,452 B2
(45) Date of Patent: *Jun. 1, 2021

(54) STEM CELL STIMULATING COMPOSITIONS AND METHODS OF TREATING MELASMA

(71) Applicant: MEDICELL TECHNOLOGIES, LLC, Carlsbad, CA (US)

(72) Inventor: Nikolay Turovets, Carlsbad, CA (US)

(73) Assignee: Medicell Technologies, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/062,864

(22) PCT Filed: Dec. 15, 2015

(86) PCT No.: PCT/US2015/065870
§ 371 (c)(1),
(2) Date: Jun. 15, 2018

(87) PCT Pub. No.: WO2017/105413
PCT Pub. Date: Jun. 22, 2017

(65) Prior Publication Data
US 2019/0022182 A1  Jan. 24, 2019

(51) Int. Cl.
| | | |
|---|---|---|
| *A61K 38/17* | (2006.01) |
| *A61Q 19/02* | (2006.01) |
| *A61K 8/64* | (2006.01) |
| *A61K 45/06* | (2006.01) |
| *A61K 9/00* | (2006.01) |
| *A61K 38/38* | (2006.01) |
| *A61K 8/65* | (2006.01) |
| *A61K 38/39* | (2006.01) |
| *A61K 38/18* | (2006.01) |
| *A61K 8/44* | (2006.01) |
| *A61K 31/198* | (2006.01) |
| *A61K 31/66* | (2006.01) |
| *A61K 8/55* | (2006.01) |
| *A61N 5/06* | (2006.01) |
| *A61M 37/00* | (2006.01) |
| *A61K 8/14* | (2006.01) |
| *A61N 5/067* | (2006.01) |

(52) U.S. Cl.
CPC ............ *A61K 38/1729* (2013.01); *A61K 8/14* (2013.01); *A61K 8/442* (2013.01); *A61K 8/553* (2013.01); *A61K 8/64* (2013.01); *A61K 8/65* (2013.01); *A61K 9/0014* (2013.01); *A61K 31/198* (2013.01); *A61K 31/66* (2013.01); *A61K 38/1808* (2013.01); *A61K 38/1825* (2013.01); *A61K 38/38* (2013.01); *A61K 38/39* (2013.01); *A61K 45/06* (2013.01); *A61M 37/0015* (2013.01); *A61M 37/0092* (2013.01); *A61N 5/062* (2013.01); *A61Q 19/02* (2013.01); *A61K 2800/91* (2013.01); *A61M 2037/0007* (2013.01); *A61M 2037/0023* (2013.01); *A61M 2037/0061* (2013.01); *A61N 2005/067* (2013.01)

(58) Field of Classification Search
CPC .......... A61M 37/0092; A61M 37/0015; A61M 2037/0061; A61M 2037/0007; A61M 2037/0023; A61K 45/06; A61K 38/39; A61K 38/38; A61K 38/1825; A61K 38/1808; A61K 38/1729; A61K 31/66; A61K 31/198; A61K 9/0014; A61K 8/65; A61K 8/553; A61K 8/442; A61K 8/64; A61K 8/14; A61K 2800/91; A61N 5/062; A61N 2005/067; A61Q 19/02
See application file for complete search history.

(56) References Cited

U.S. PATENT DOCUMENTS

| | | | | |
|---|---|---|---|---|
| 2004/0091493 | A1* | 5/2004 | Perrier | A61K 8/365 424/184.1 |
| 2005/0277176 | A1* | 12/2005 | McCray, Jr. | C07K 14/4723 435/69.1 |
| 2006/0115480 | A1* | 6/2006 | Hillman | A61P 1/00 424/146.1 |
| 2008/0050398 | A1* | 2/2008 | Bockmuehl | A61K 38/1709 424/190.1 |

FOREIGN PATENT DOCUMENTS

| | | |
|---|---|---|
| WO | 2011009757 | 1/2011 |
| WO | 2011109469 | 9/2011 |
| WO | 2014004339 | 1/2014 |
| WO | 2015195677 | 12/2018 |

OTHER PUBLICATIONS

Handel et al. An Bras Dermatol., 2014, 89(5): 771-82. (Year: 2014).*

(Continued)

*Primary Examiner* — Doan T Phan

(74) *Attorney, Agent, or Firm* — Fish IP Law, LLP

(57) ABSTRACT

Compositions and methods for topical treatment of the hyperpigmented lesions of melasma are presented. Such compositions include defensins in concentrations that are below those that exhibit antimicrobial activity, and can be in the form of a topically applied gel, lotion, wash, shampoo, cream, or mask. Various formulations for such compositions, which can include various pharmaceutically acceptable stabilizers, emollients, and fragrances, are provided.

9 Claims, 2 Drawing Sheets

(56) References Cited

OTHER PUBLICATIONS

PCT Search Report & Written Opinion dated Sep. 13, 2016 for PCT/US2015/065870 entitled Stem Cell Stimulating Compositions and Methods of Treating Melasma filed on Dec. 15, 2015.

Lough, Denver et al, Stimulation of the follicular bulge LGR5+ and LGR6+ stem cells with the gut-derived human alpha defensin 5 results in decreased bacterial presence, enhanced wound healing, and hair growth from tissues devoid of adnexal structures; Plast Reconstr Surg. Nov. 2013;132(5):1159-71.

Candille at al, Science, Candille at al, A β-Defensin Mutation Causes Black Coat Color in Domestic Dogs, Science Nov. 30, 2007; 318(5855): 1418-1423.

* cited by examiner

Before treatment

After 6 weeks of treatment

 
Fig. 2A                    Fig. 2B

STEM CELL STIMULATING COMPOSITIONS AND METHODS OF TREATING MELASMA

FIELD OF THE INVENTION

The field of the invention is topical cosmetic formulations useful in the treatment of melasma.

BACKGROUND

The following background discussion includes information that may be useful in understanding the present invention. It is not an admission that any of the information provided herein is prior art or relevant to the presently claimed invention, or that any publication specifically or implicitly referenced is prior art.

Melasma is characterized by the development of well demarcated brown or gray-brown patches of hyperpigmentation, typically on the skin of the forehead, cheeks, and upper lip (although such hyperpigmented patches can appear elsewhere on the body). Development of these dark patches is more common in women, and is often associated with pregnancy, the use of hormonal contraceptives, and hormone replacement therapy. The development of melasma also appears to be associated with sun exposure, being most common in women with light brown skin coloration living in sunny climates.

Although melasma is harmless, the appearance of these dark patches is considered to be cosmetically unappealing and can be a source of distress. While the appearance of melasma can be reduced using camouflage makeup, such an approach requires considerable skill and effort, and may need to be repeated throughout the day. In many instances melasma will resolve spontaneously on discontinuation of hormonal treatments, avoiding sun exposure, and application of sun block. Currently, melasma is generally treated using topically applied depigmenting agents (such as hydroquinone), chemical agents that alter the activity of melanocytes, chemical or mechanical "peels" that remove the affected skin surface, and laser treatment. Unfortunately some of these treatments cannot be utilized during pregnancy. In addition reoccurrence is common, particularly following sun exposure.

Since their initial discovery in the 1960's, there has been much research surrounding the role of defensins. Defensins are small cysteine-rich proteins, usually only 14-85 amino acids long. Defensins can be found in invertebrates, vertebrates, and plants, and have been shown to be active against many bacteria, fungi, and viruses. In fact, much of the body of research has focused on the antimicrobial properties of defensins. However, in recent years, some research has explored other roles defensins may play in human skin, such as in wound healing or hair growth.

PCT Patent Application WO 2014/004339 A2 by Applicant ELC Management LLC teaches the use of a resveratrol-containing cosmetic composition to stimulate endogenous production of cellular beta defensins in skin cells. In order to illustrate this effect, the inventors tested the composition on Normal Human Epidermal Keratinocytes ("NHEK") in vitro and measured the presence of beta defensin in NHEK. The resulting stimulated quantities of defensin were very small (approximately 0.001 ng/ml). The inventors theorized that the stimulation of beta defensins in keratinocytes by resveratrol-containing compositions would be effective for treating acne, inhibiting microbial growth on the skin, and improving skin barrier repair. Because of the low stimulated quantities of beta defensin, and because the compositions do not actually contain defensins, it is questionable that these compositions would produce cosmetically meaningful results. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

On the other hand, defensins have been shown to play a significant role in wound healing. In the journal article titled "Stimulation of the follicular bulge LGR5+ and LGR6+ stem cells with the gut-derived human alpha defensin 5 results in decreased bacterial presence, enhanced wound healing, and hair growth from tissues devoid of adnexal structures" (Plast. Reconstr. Surg. 2013; 132(5):1159-71), Lough et al. report a human alpha defensin 5-containing formulation that was shown under experimental conditions to recruit LGR5+ and LGR6+ stem cells to third-degree burns in mice, which accelerated healing of the wound. However, these findings leave many questions. For example, in the experimental conditions described by Lough et al., it is unclear if LGR5+ and LGR6+ were activated by pro-inflammatory conditions and other factors already present in the wound or due to the topical application of defensins. Furthermore, the wound healing formulation used by Lough et al. contained concentrations of defensins at antimicrobially active concentrations (e.g. about 105 ng/ml). However, this high concentration of defensin may make any resulting cosmetic composition more allergenic and more costly.

Therefore, even though defensin containing and defensin stimulating compositions are known, there is a need for a cosmetic topical formulation that are effective in reducing or eliminating the occurrence and/or appearance of melasma.

SUMMARY OF THE INVENTION

The inventive subject matter is directed towards various topical formulations, methods of manufacture of the topical formulation in which the topical formulation includes antimicrobially effective or sub-antimicrobially effective concentrations of at least one defensin, and methods of applying the topical formulation to the healthy skin of users to reduce or eliminate the appearance of melasma (for example, epidermal melasma).

In one aspect of the invention, a topical cosmetic formulation includes a defensin in a cosmetically acceptable carrier. Preferred topical cosmetic formulations are ready-to-use and contain the defensin at a sub-antimicrobially effective concentration, wherein the concentration is ineffective to inhibit growth of a microbial pathogen in a therapeutically effective manner but is effective in reducing or eliminating the appearance of melasma. Still further preferred topical formulations may further comprise a blend of two or more different defensins, wherein the combined concentration of defensins in the formulation is a sub-antimicrobially effective concentration.

The inventors further contemplate methods of using defensins at antimicrobially effective or sub-antimicrobially effective concentrations in topical formulations to recruit LGR6+ stem cells to an interfollicular space in non-injured skin. It should be appreciated that methods of recruiting LGR6+ stem cells may include a step of providing a topical formulation containing a sub-antimicrobial concentration of at least one defensin and a further step of applying the formulation to non-injured skin to reduce or eliminate the appearance of melasma and/or a treated melasma lesion.

It is preferred that the inventive compositions, methods, and uses employ at least one of alpha-defensin 1, alpha-defensin 5, alpha-defensin 6, neutrophil defensin 1, neutrophil defensin 2, neutrophil defensin 3, neutrophil defensin 4, theta-defensin, beta-defensin 1, beta-defensin 2, beta-defensin 3, and beta-defensin 4. In especially preferred topical compositions and methods, alpha-defensin 5 and beta-defensin 3 are employed. It should be appreciated that the defensin can comprise a synthetic defensin, a human defensin, recombinant defensin, a primate defensin, a murine defensin, a caprine defensin, a bovine defensin, an ovine defensin, an equine defensin, a lapine defensin, a porcine defensin, a canine defensin, and/or a feline defensin.

With respect to the sub-antimicrobially effective concentration of the first defensin in the ready-to-use topical cosmetic formulation, contemplated concentrations may be between 0.01 and 100 ng/ml, or between 1 and 30 ng/ml, including the end points of each range. Additionally, especially preferred embodiments of the inventive subject matter employ defensin concentrations of about 22 ng/ml and about 4.4 ng/ml in ready-to-use formulations.

The inventors unexpectedly found that, even at these low concentrations, defensins can be effective to substantially reduce the appearance of melasma and/or a treated melasma lesion. Without wishing to be bound by any particular theory, the effectiveness of defensins at these sub-antimicrobially effective concentrations may be due to the activation and/or recruitment of LGR6+ stem cells. Typically, defensins used in preferred embodiments of the inventive subject matter have a purity greater than 95% as shown by HPLC, and the sequence and proper disulfide bond formation of the defensins can be confirmed by tandem MS/MS.

Depending on the nature of the topical formulation, it should be recognized that defensins may be encapsulated in liposomes or other nanoparticles. In preferred formulations, defensins may also be associated with a carrier, in particular a protein carrier such as albumin (e.g., human serum albumin, bovine serum albumin, egg albumin, and recombinant albumin produced by rice, other plants, bacteria or yeast), also encapsulated in liposomes where desirable.

The inventors further contemplate that the topical cosmetic formulations may also include supplements to provide nutrition and support for LGR6+ stem cells. Typical supplements include human serum albumin, bovine serum albumin, egg albumin (i.e. ovalbumin), recombinant albumin produced by rice, other plants, bacteria or yeast, plant hydrolysate, beta-cyclodextrin, glutamine, phospholipids, fibronectin, hyaluronate, hyaluronic acid, plant hydrolysate, L-alanyl-L-glutamine, gelatin, recombinant gelatin, Epidermal Growth Factor (EGF), vitamin E, Tocopheryl Nicotinate, ubiquinone, coenzyme Q10, and/or an antioxidant. Suitable cosmetic formulations can also incorporate an ultraviolet and/or visible light blocking or screening agent.

The inventors have appreciated that the topical cosmetic formulations of the inventive subject matter can be included in kits with exfoliating masks. Especially preferred kits include a mask, a cream treatment formulation, and a serum treatment formulation.

Further aspects of the inventive subject matter provide methods of treating scars, sunburn, bruises, and other skin disorders in which the epidermal layers of the skin are largely intact. Exemplary methods include the steps of providing a topical formulation having at least one defensin at a sub-antimicrobially effective concentration and applying the formulation to non-injured skin under a protocol effective to substantially reduce the appearance of melasma an/or a treated melasma lesion.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1A shows the appearance of the skin prior to treatment. FIG. 1B shows the appearance of the skin following treatment.

FIGS. 2A and 2B show side-by-side photographs that show a reduction in the appearance of brown spots. FIG. 2A shows the appearance of the skin prior to treatment. FIG. 2B shows the appearance of the skin following treatment.

DETAILED DESCRIPTION

Figure 1A:
FIGS. 1A and 1B show side-by-side photographs that show reduction in wrinkles.

The inventors unexpectedly discovered that antimicrobal and sub-antimicrobial concentrations of defensins can achieve numerous desirable effects on non-injured skin when applied in ready-to-use topical formulations. Among other things, such topical formulations provide a significant reduction or elimination of the occurrence and/or appearance of the hyperpigmented lesions characteristic of melasma, for example epidermal melasma.

In one preferred embodiment, a ready-to-use topical cosmetic formulation comprises at least one defensin present in a topical cosmetic formulation at a sub-antimicrobially effective concentration. Of course it should be appreciated that topical formulations may contain one defensin, a combination of two defensins, or a combination of three or more defensins. The defensins used may be of the same or different types and subtypes. For example suitable defensins may include one or more of alpha-defensin 1, alpha-defensin 5, alpha-defensin 6, neutrophil defensin 1, neutrophil defensin 2, neutrophil defensin 3, neutrophil defensin 4, theta-defensin, beta-defensin 1, beta-defensin 2, beta-defensin 3, and beta-defensin 4. Especially preferred topical formulations contain alpha-defensin 5 and beta-defensin 3. When two more defensins are used in combination, each defensin may be present in equal quantities by mass or at mass ratios specified to achieve a desired result, such as 1:1.5, 1:2, 1:4, 1:5, etc. Notably, it should be appreciated that the total concentrations of defensins used in contemplated ready-to-use formulations are ineffective at inhibiting substantial proliferation of microbes in established skin infections in a therapeutically effective manner. Alternatively, in other embodiments of the inventive concept the concentration of defensin or defensins comprising the formulation can be sufficient to have an anti-microbial effect.

As used herein, the term "ready-to-use" indicates that the defensin-containing topical formulation is in a form that is presented for sale and application. It is contemplated that ready-to-use formulations can comprise a fully combined solution, cream, gel, serum, lotion, etc. Alternatively, the defensin can be packaged in a separate container (e.g., in a vial that pumps a defensin solution with a cream that the user blends before applying to unbroken skin) and combined with another topical formulation at the time of use/application.

As also used herein, the phrase "sub-antimicrobially effective concentration" means concentration(s) of defensins which are characterized by an inability to inhibit the proliferation of microbes in an established infection. Typically, ready-to-use topical formulations do not include concentrations greater than 1 µg/ml. In preferred embodiments, the concentration of defensins lies between about 0.01 and about 100 ng/ml, and even more typically between about 1 and about 30 ng/ml, wherein contemplated concentrations include the end points of each range. In even more preferred embodiments, the topical cosmetic formulations have defensin concentrations of about 22 ng/ml and about 4.4 ng/ml. As used herein, when the term "about" is used in conjunction with a numeral, "about" means a range of plus or minus ten percent of the numerical value given, including end points. The recitation of ranges of values herein is merely intended to serve as a shorthand method of referring individually to each separate value falling within the range. Unless otherwise indicated herein, each individual value is incorporated into the specification as if it were individually recited herein.

General topical formulations can include any and all formulations suitable for cosmetic topical use, especially on non-injured skin. As used herein, the term "non-injured" skin refers to skin in which dermis and hypodermis are substantially intact. Therefore, viewed from a different perspective, non-injured skin will appear intact to the unaided eye, with no breach sufficiently large or deep to result in bleeding. Thus, non-injured (or "healthy") skin includes aged skin and skin with first degree sunburn, environmental exposure, bruising, or partially ablated stratum corneum. Non-injured (or healthy) skin also excludes skin displaying persistent infection with pathogens that result in visible symptoms and signs of infection.

With respect to the source of defensins, the inventors contemplate that defensins from both natural and synthetic sources may be suitable for incorporation into topical formulations. For example, defensins may be obtained from plants (e.g., *Arabidopsis*, pea, tobacco, spruce, and/or recombinant plants), mammals or other animals, recombinant organisms (such as yeast or bacteria), and/or products of laboratory peptide synthesis (for example, through the use of a Merrifield resin or other solid-phase synthesis). Exemplary defensins derived from natural sources may include human defensins, simian defensins, murine defensins, bovine defensins, ovine defensins, caprine defensins, equine defensins, lapine defensins, porcine defensins, canine defensins, and/or feline defensins.

Due to their relatively low quantities in a living organism and low molecular weight, it is generally preferred, however, that the defensins are synthetic defensins. Synthetic defensins include defensins produced by chemical synthesis (e.g., solid phase synthesis) or by recombinant technologies (e.g., produced by recombinant bacteria, yeast, tissue cultures, plants or animals). The inventors further contemplate that defensin analogues such as hapivirins and diprovirins may be used in some embodiments of the inventive subject matter. Still further, the inventors further contemplate that the defensins can also be modified to increase their activity and specificity for cosmetic improvements to the appearance of skin. For example, defensins may be unfolded and refolded under controlled conditions to ascertain proper disulfide bond formation (which can be monitored by MS analysis and/or CD spectroscopy). Alternatively, chemical modifications (e.g., using non-natural amino acids and/or PEGylation to increase half-life time, or derivatized proteinogenic amino acids to increase lipophilicity) are contemplated to tailor the defensins to a particular need.

Regardless of the source of the defensins, it should be appreciated that specific activity of defensins is dependent on various factors, including isomeric form and tertiary structure of the final protein. Thus, and especially where the defensin is synthetic, orthogonal protecting groups can be used to protect selected cysteine residues, which can then be individually deprotected and bonded with the matching target cysteine residue, leading to coordinated non-random disulfide bond formation. Use of such protecting groups in the synthetic strategy can give rise to defensins with a specific activity that is comparable to the specific activity of the native defensin. Any suitable characterization and quality control measures may be employed. Typically, the specific activity of defensins incorporated into the inventive topical formulations is measured by purity as determined by HPLC. In exemplary embodiments, the defensin is between about 80% and about 100% pure, more typically the defensin is at least about 90% pure, or at least about 95% pure, or at least about 99% pure, or at least about 99.9% pure. Additionally, proper amino acid sequence and disulfide bond formation can be confirmed by tandem MS/MS, for example.

With respect to suitable concentration of defensins in cosmetic formulations presented herein, it is contemplated that all concentrations are deemed appropriate so long as such concentrations are cosmetically effective in reducing the appearance and/or occurrence of hyperpigmented regions characteristic of melasma on healthy skin. Consequently, the total concentration of defensins (single type or combination of distinct defensins) in the final cosmetic formulation as applied to the skin can be between about 0.01 ng/ml and about 100 ng/ml, or between about 0.1 ng/ml and about 100 ng/ml, or between about 1 ng/ml and about 100 ng/ml, or between about 2 ng/ml and about 80 ng/ml, or between about 4 ng/ml and about 60 ng/ml, or between about 1 ng/ml and about 30 ng/ml. Thus, preferred compositions include defensins at a concentration of at least about 0.01 ng/ml, at least about 0.1 ng/ml, at least about 1 ng/ml, or at least about 4 ng/ml, but no more than about 200 ng/ml, no more than about 100 ng/ml, no more than about 75 ng/ml, or no more than about 50 ng/ml.

In some embodiments the defensin can be associated with a cosmetically acceptable protein to increase stability and/or delivery characteristics. In this context, it should be appreciated that such an association is preferably non-covalent (e.g., electrostatic, ionic, hydrophobic, etc.), however, covalent attachment to a side group of the protein is not excluded. Exemplary cosmetically acceptable proteins include lactoferrin, transferrin, and albumin (e.g., human serum albumin, bovine serum albumin, ovalbumin, and/or recombinant albumin). The defensins and protein carriers can be in various ratios, including equimolar, sub-, and supramolar ratios. Additionally, combinations of two or more protein carriers can be used. For example, in a formulation in which two defensins are used, one defensin may be associated with one carrier, and the other defensin may be associated with a different carrier. Therefore, any combination of defensins and carriers is contemplated.

In still further contemplated aspects, the defensins (and carrier proteins) can be encapsulated in cosmetically acceptable formulations, and especially formulations using a lipid membrane. For example, liposomes, microcapsules, nanocapsules, microparticles, nanoparticles, microparticle delivery systems, are especially contemplated. A description of some cosmetically acceptable cosmetic delivery systems can be found in Maherani et al, "Liposomes: A Review of Manufacturing Techniques and Targeting Strategy," Current Nanoscience; 7:436-452 (2011). A preferred method of liposome manufacturing is a shear method. Preferred cosmetic delivery systems resemble naturally occurring membranes, are flexible, and can penetrate interstitial spaces between cells. It is further contemplated that cosmetic delivery systems may have monolayer, bilayer (e.g. unilamellar vesicle or ULV), or multi layer structures (e.g. multilamellar vesicle or MLV). Additionally, multilayer liposomes, microcapsules, microsomes, and nanocapsules can have nested structures (e.g. multivesicular vesicle or MVV). Cosmetic delivery systems used in the topical formulations can range in size from about 500 nm to about 10 μm. In the preparation of cosmetic delivery systems, all cosmetically acceptable lipid compositions are contemplated, especially pharmaceutically acceptable lipids. In most instances preferred cosmetic delivery systems comprise amphipathic or amphiphilic molecules such as phospholipids or combinations of phospholipids (e.g., phosphatidylcholine, phosphatidylethanolamine, phosphatidic acid, phosphatidylserine, and phosphoinositides). Additionally, in some instances contemplated cosmetic delivery systems can contain additive(s) such as sterols, polyethylene glycol, cholesterol, dicethylphosphate, stearyl amine, etc. With respect to the amount of delivery systems incorporated in each ready-to-use formulation, the cosmetic delivery system content will typically be adjusted to achieve a sub-antimicrobial concentration of defensins within a preferred range. Unilamellar vesicles/liposomes can be produced using high shear techniques. These vesicles have a greater Zeta Potential than the typical liposome, which allows for smaller, more uniform particle size with increased stability. Zeta Potential is an indicator of the electronic charge on the surface of any macroscopic material that is in contact with a liquid. This can be used to predict and control the stability of suspensions; the higher the Zeta Potential, the greater the stability of the molecule because the charged particles are able to repel and overcome their innate affinity to assemble.

It should be noted that defensins, protein carriers, liposomes, or other membranaceous structures have a molecular weight that exceeds transmembrane delivery, and even delivery across the stratum corneum. Nevertheless, as is discussed in more detail, the defensins have a profound effect on stem cell activity in dermal and hypodermal layers. While not wishing to be bound by any theory or hypothesis, the inventors contemplate that the liposomal formulations have the ability to transport the defensins via an interstitial route and/or to invade the hair follicle to a depth and concentration sufficient to activate LGR6+ cells. Viewed from another perspective, the use of cosmetic delivery systems is thought to aid in the delivery of defensins as one would not expect defensins per se to penetrate the stratum corneum of the skin (acting as a barrier to molecules with molecular weights greater than 500 Da). Moreover, when associated with albumin (65-70 kDa) and/or liposomes, it becomes at least conceptually even more difficult for the defensin composition to penetrate unbroken skin. Thus, the inventors hypothesize that the mechanism for delivering defensins is different in unbroken skin when compared with broken or injured skin.

In some embodiments of the inventive concept a formulation that includes one or more defensins can be delivered by an active mechanism. Suitable active mechanisms can include application of laser energy, acoustic pressure wave, ultrasound, microneedles, and/or injections to the skin area undergoing treatment, in order to facilitate transport of the defensins to the desired region of the skin and/or skin-associated (i.e. epidermis, dermis, basal layer, and/or hair follicle) area(s).

In another aspect, the inventors advantageously provide additional ingredients that nourish and support the recruited stem cells in healthy skin. For example, albumin (e.g., human serum albumin, bovine serum albumin), egg albumin (ovalbumin), recombinant albumin, plant hydrolysate, and β-cyclodextrin, glutamine, phospholipids (liposomes), fibronectin, hyaluronate, plant hydrolysate, L-alanyl-L-glutamine, gelatin, Vitamin E (tocopheryl nicotinate), ubiquinone (coenzyme Q10), gelatin, recombinant gelatin, hyaluronic acid, Epidermal Growth Factor can provide nutrition and support to the stem cells.

In yet further contemplated aspects, cosmetic treatment of melasma on healthy skin can be further be assisted by supplemental procedures. Especially contemplated procedures include chemical and/or mechanical exfoliation. For example, chemical exfoliation may be performed using one or more proteases (for example papain, *Lactobacillus*/Pumpkin Ferment Extract, *Lactobacillus/Punica Granatum* Fruit Ferment Extract), alpha-hydroxy acids, etc. while mechanical exfoliation may be performed using sugar crystals, cellulosic plant matter, tape stripping, frozen $CO_2$, polymeric beads, and/or silica granules.

Although not wishing to be bound by theory, the inventors contemplate that the inventive subject matter (i.e., methods and use of antimacribic ally effective or sub-antimicrobially active concentrations of defensins in topical cosmetic formulations) can act to recruit LGR6+ stem cells to the interfollicular space in non-injured skin. Most typically, a user will be instructed to apply the topical formulation to regions of non-injured skin that include or are likely to include hyperpigmented areas characteristic of melasma under a protocol effective to reduce or eliminate the appearance of hyperpigmented areas of skin, and/or effective to reduce or eliminate the occurrence of at such hyperpigmented areas. For example, defensins can be applied at least once daily (or twice daily) for a period of at least one week, or two weeks, three weeks, six weeks, or even longer. Beneficially, the total quantity of applied formulations is such that the formulation is absorbed into the skin. For example, topical formulations are typically applied at about 0.1 to about 500 mg per $cm^2$, about 0.1 to about 500 mg per $cm^2$, about 0.5 to about 300 mg per $cm^2$, about 5 to about 500 mg per $cm^2$, or about 100 to about 500 mg per $cm^2$.

Using topical compositions such as those presented in the examples below, the inventors discovered that cosmetic formulations that included the defensins are effecting in reducing the appearance and/or preventing the occurrence or reoccurrence of hyperpigmented lesions associated with melasma.

In some embodiments of the inventive concept, topical application of such defensin formulations on a suitable schedule is sufficient to reduce the area of a treated melasma lesion to less than 90%, 80%, 70%, 60%, 50%, 40%, 30%, 20%, 10%, 5%, or less than 5% of the melasma lesion prior to treatment with the topical defensin formulation. In other embodiments of the inventive concept, topical application of such a defensin formulation on a suitable schedule can reduce excessive pigmentation associated with a treated melasma lesion to less than 300%, 200%, 100%, 50%, 25%, or 10% of pigmentation beyond that associated with normal, unaffected skin adjacent to the treated melasma lesion.

In suitable treatment protocols the defensin formulation can be applied four times a day (e.g. every 6 hours), three times a day (e.g. every 8 hours), twice a day (e.g. every 12 hours), once a day (e.g. in the morning, or prior to ultraviolet exposure), every other day, every three days, once a week, or at a frequency determined through practical use. In some embodiments the topical defensin formulation can be applied more frequently at the beginning of treatment. In other embodiments the topical defensin formulation can be applied more frequently as treatment progresses. In still other embodiments treatment can continue on a first treatment schedule until the appearance of the melasma lesion is completely resolved, acceptable, and/or is stabilized and improved, and then switched to a second treatment schedule that maintains the treated appearance.

Treatment with the taught topical defensin formulations can be carried out for any period of time suitable to eliminate or reduce the appearance of a melasma lesion. Suitable treatment periods can be at least a week, 2 weeks, 3 weeks, 4 weeks, 6 weeks, 8 weeks, 3 months, 4 months, 5 months, 6 months, or longer. In some embodiments a topical defensin formulation can be applied on a long term (i.e. greater than one year) or for an open ended time period on a maintenance schedule suitable to provide and maintain the desired reduction or elimination in the appearance of a treated melasma lesion.

EXAMPLES

Suitable formulations are described in International Patent Application No. PCT/US15/36049, which is incorporated herein by reference. While suitable cosmetic formulations may be prepared using any number of ingredients and formulations known in the art, preferred topical formulations include those that are ready-to-use and can be applied by a user. Therefore, with respect to cosmetically acceptable carriers, all cosmetically acceptable carriers are contemplated and include creams, oil-in-water emulsions, water-in-oil emulsions, foams, mousses, ointments, lotions, suspensions, serum, and gels. In some embodiments the cosmetic formulation can include a sunscreen, such as an ultraviolet and/or visible light blocking ingredient (for example, zinc oxide), which advantageously reduces the impact of a suspected causative factor in the development of melasma.

Examples of suitable topical cosmetic cream formulations can include one or more of the following ingredients: water, *Carthamus tinctorius* (safflower) oleosomes, *Butyrospermum parkii* (Shea) Butter, *Macadamia integrifolia* seed oil, niacinamide, yeast extract, ammonium acryloyldimethyltaurate/VP copolymer, *Helianthus annuus* (sunflower) seed oil, phospholipids, alpha-defensin 5, beta-defensin 3, hyaluronic acid, *Ophiopogon japonicus* root extract, hydrolyzed *Candida saitoana* extract, sea whip extract, *Lycium chinense* fruit extract, *Vaccinium angustifolium* fruit extract, *Vaccinium marcrocarpon* (cranberry) fruit extraubiquinone, L-alanyl-L-glutamine, *Leuconostoc*/Radish root ferment filtrate, gelatin, SH oligopeptide-1, xanthan gum, phytic acid, polysorbate 20, caprylic/capric triglyceride, phenoxyethanol, caprylyl glycol, ethylhexylglycerin, hexylene glycol, potassium sorbate, sodium chloride, and natural and/or artificial fragrance.

Examples of a suitable topical cosmetic serum formulation can include one or more of the following: water, cyclopentasiloxane, glycerin, niacinamide, *Sinorhizobium meliloti* ferment filtrate, dimethicone, polysorbate 20, dimethicone/vinyl dimethicone crosspolymer, lauryl PEG-9 polydimethylsiloxyethyl dimethicone, ammonium acryloyldimethyltaurate/VP copolymer, phospholipids, alpha-defensin 5, beta-defensin 3, palmitoyl tripeptide-38, sodium hyaluronate, *Arabidopsis thaliana* extract, sea whip extract, ergothioneine, *Helianthus annuus* (sunflower) seed oil, *Rosmarinus offinalis* (rosemary) leaf extract, SH oligopeptide-1, tocopheryl acetate, ubiquinone, *Leuconostoc*/radish root ferment filtrate, albumin, gelatin, L-alanyl-L-glutamine, caprylic/capric triglyceride, cetyl hydroxyethylcellulose, lecithin, hydroxypropyl cyclodextrin, phytic acid, phenoxyethanol, caprylyl glycol, ethylhexylglycerin, hexylene glycol, and/or sodium chloride.

Examples of a suitable mask formulation can include one or more of the following: butylene glycol, PEG-8, tapioca starch, sucrose, titanium dioxide, hydroxyethyl acrylate/sodium acryloyldimethyl taurate copolymer, squalane, polysorbate 60, *Carica papaya* (papaya) fruit, papain, *Aloe barbadensis* leaf juice, *Lactobacillus*/pumpkin ferment extract, *Lactobacillus/Punica granatum* fruit germent extract, sea whip extract, *Cananga odorata* flower oil, *Citrus aurantium dulcis* (orange) peel oil, caprylic/capric triglyceride, lactic acid, phenoxyethanol, caprylyl glycol, ethylhexylglycerin, and/or hexylene glycol.

Liposome Formulations

Table 1 below shows an exemplary cosmetic delivery liposome formulation including two types of defensins. These liposomes are typically incorporated into a cosmetic formulation at a fraction of about 1.0 wt % to 10.0 wt % for most skin care applications. In some embodiments defensin concentration can be up to 10 mg/ml or higher.

TABLE 1

Exemplary Liposome Formulation

| Component | Concentration |
| --- | --- |
| Water (protease-free) | to 100% |
| Albumin | 0.1-1.0 mg/ml |
| L-alanyl-L-glutamine | 0.1-1.0 mg/ml |
| Gelatin | 2-200 µg/ml |
| Matrix proteins | 1-100 ng/ml |
| Human alpha-defensin 5 | 1-200 ng/ml |
| Human beta-defensin 3 | 1-200 ng/ml |
| Growth factors (e.g., EGF, FGF-2/ with or without) | 0.1-100 ng/ml |
| Phospholipids | 2-20 wt % |
| Antioxidants | 0.3-3 wt % |

In yet a further aspect of the inventive subject matter, topical cosmetic formulations can be offered together as a kit. Preferred kits include a mask formulation and a defensin-containing cream or serum treatment formulation. Even more preferred kits include a mask formulation and both the defensin-containing cream and serum treatment formulations.

In the manufacture of cosmetic defensin formulations, it is contemplated that concentrated defensin preparations can be added to cosmetic base formulations such that the concentration of the defensin in the ready-to-use product is at a targeted sub-antimicrobially effective concentration. Depending on the desired formulation, defensins can be incorporated into concentrated preparations as solutions, associated with carrier proteins, and more typically as liposomal formulations. Such concentrated defensin preparations can be added to the cosmetic base formulations in proportions as given below:

Exemplary Body Lotion (Oil-in-Water) Formulation:

| Mixture a) | PEG-7 hydrogenated castor oil | 2.00% |
| --- | --- | --- |
| | PEG-20 glyceryl laurate | 1.00% |
| | cocoglycerides | 3.00% |
| | cetearyl alcohol | 1.00% |
| | cetearyl isononanoate | 4.00% |
| | octyl stearate | 4.00% |
| | phenoxyethanol, methylparaben, | 0.30% |

|          |                                                                                                                   |         |
|----------|-------------------------------------------------------------------------------------------------------------------|---------|
|          | ethylparaben, butylparaben, propylparaben, isobutylparaben                                                         |         |
| Mixture b) | water, distilled                                                                                                | 73.40%  |
|          | phenoxyethanol, methylparaben, ethylparaben, butylparaben, propylparaben, isobutylparaben                          | 0.30%   |
|          | glycerin                                                                                                           | 3.00%   |
| Mixture c) | concentrated defensin preparation                                                                               | 5.00%   |
| Mixture d) | acrylamides copolymer, mineral oil C13-C14 isoparaffin, polysorbate 85                                          | 3.00%   |

To prepare the body lotion formulation mixture a) is melted at approximately 70° C. Mixture b) is heated to approximately 70° C. and then added to mixture a) while stirring. Stirring is continued until the lotion has cooled down to approximately 30 C°. Mixtures c) and d) are added to the cooled mixture while stirring, and the lotion is homogenized. In some embodiments final defensin concentration can range from 1 ng/ml to 10 mg/ml or higher.

Exemplary Gel-Lotion Formulation:

|            |                                                                                                                 |         |
|------------|-----------------------------------------------------------------------------------------------------------------|---------|
| Mixture a) | acrylamides copolymer, mineral oil, C13-14 isoparaffin, polysorbate 85                                          | 5.00%   |
|            | myreth-3 myristate                                                                                               | 4.00%   |
| Mixture b) | water, distilled                                                                                                | 85.00%  |
|            | phenoxyethanol (and) methylparaben (and) ethylparaben (and) butylparaben (and) propylparaben (and) isobutylparaben | 0.50%   |
|            | xanthan gum                                                                                                      | 0.50%   |
| Mixture c) | concentrated defensin preparation                                                                                | 5.00%   |

To prepare the gel lotion formulation mixture a) is dissolved at approximately 50° C. Mixture b) is dispersed at room temperature and added to mixture a) while stirring. Then, mixture c) is added while stirring.

Exemplary Oil-in-Water Cream Formulation:

|            |                                                                                                                   |         |
|------------|-------------------------------------------------------------------------------------------------------------------|---------|
| Mixture a) | cetearyl alcohol (and) ceteareth-20                                                                                | 8.00%   |
|            | cocoglycerides                                                                                                    | 2.00%   |
|            | cetearyl alcohol                                                                                                  | 2.00%   |
|            | dicaprylyl ether                                                                                                  | 8.00%   |
|            | oleyl erucate                                                                                                     | 7.00%   |
|            | phenoxyethanol, methylparaben, ethylparaben, butylparaben, propylparaben, isobutylparaben                          | 0.30%   |
| Mixture b) | water, distilled                                                                                                  | 62.40%  |
|            | phenoxyethanol, methylparaben, ethylparaben, butylparaben, propylparaben, isobutylparaben                          | 0.30%   |
|            | glycerin                                                                                                          | 5.00%   |
| Mixture c) | concentrated defensin preparation                                                                                 | 5.00%   |

To prepare the formulation mixture a) is melted at approximately 70° C. Mixture b) is heated to approximately 70° C. and added to mixture a) while stirring. Stirring is continued until the cream has cooled to approximately 30° C. Then, composition c) is added while stirring and the cream is homogenized. In some embodiments final defensin concentration can range from 1 ng/ml to 10 mg/ml or higher.

Exemplary Water-in-Oil Cream Formulation:

|            |                                                          |        |
|------------|----------------------------------------------------------|--------|
| Mixture a) | diisostearoyl polyglyceryl-3 dimer dilinoleate           | 3.00%  |
|            | beeswax                                                  | 0.60%  |
|            | castor oil, hydrated                                     | 0.40%  |
|            | paraffinum subliquidum                                   | 5.00%  |
|            | isohexadecane                                            | 10.00% |
|            | PPG-15 stearyl ether                                     | 2.00%  |
|            | dimethicone                                              | 0.50%  |
|            | phenoxyethanol, methylparaben, ethylparaben, butylparaben, propylparaben, isobutyparaben | 0.30%  |
| Mixture b) | water, distilled                                         | 68.40% |
|            | phenoxyethanol, methylparaben, ethylparaben, butylparaben, propylparaben, isobutylparaben | 0.30%  |
|            | glycerin                                                 | 3.00%  |
|            | MgSO$_4$*7H$_2$O                                         | 1.00%  |
| Mixture c) | concentrated defensin preparation                        | 5.00%  |
| Mixture d) | silica dimethyl silylate                                 | 0.50%  |

To prepare the oil in water cream formulation mixture a) is heated to approximately 80° C. Mixture b) is brought to 80° C. and then added to mixture a) while stirring. Stirring is continued until the cream has cooled down to approximately 30° C., then mixtures c) and d) are added and the cream is homogenized. In some embodiments final defensin concentration can range from 1 ng/ml to 10 mg/ml or higher.

Exemplary Shampoo Formulation:

| |  |
|---|---|
| Sodium polyoxyethylene lauryl ether sulfate | 15.0% |
| Alkyl polyglucoside | 4.0% |
| N-ethanol-N-methyl dodecanoic acid amide | 3.0% |
| EDTA-Na$_2$ | 0.3% |
| Malic acid to adjust pH to 6.0 | q.s. |
| Preservative | 0.5% |
| Concentrated defensin preparation | 10.0% |
| Purified water | balance |
| Total | 100.0% |

To prepare the shampoo formulation all ingredients are mixed together and the volume is brought to about 90 ml. The pH is then adjusted and the volume is finally adjusted to 100 ml (all percentages are weight %). In some embodiments final defensin concentration can range from 1 ng/ml to 10 mg/ml or higher.

Exemplary Body Wash Formulation:

| |  |
|---|---|
| Sodium polyoxyethylene lauryl ether sulfate | 16.0% |
| Sodium polyoxyethylene | 5.0% |
| N-ethanol-N-methyl palm kernel oil fatty acid amide | 2.5% |
| Glycerin | 3.0% |
| Cationized cellulose | 0.1% |
| Ethylene glycol distearate | 3.0% |
| EDTA-Na$_2$ | 0.3% |
| Citric acid to adjust pH to 5.7 | q.s. |
| Preservative | 0.5% |
| Concentrated defensin preparation | 7.5% |
| Purified water | balance |
| Total | 100.0 |

To prepare the body wash formulation all ingredients are mixed together and the volume is brought to about 90 ml. The pH is then adjusted and the volume is finally adjusted to 100 ml (all percentages are weight %). In some embodiments final defensin concentration can range from 1 ng/ml to 10 mg/ml or higher.

Exemplary Face Wash Formulation:

| |  |
|---|---|
| Sodium polyoxyethylene lauryl ether sulfate | 20.0% |
| N-ethanol-N-methyl dodecanoic acid amide | 4.8% |
| Glycerin | 3.0% |

-continued

| | |
|---|---|
| Hydroxyethyl cellulose | 0.3% |
| Ethylene glycol distearate | 1.5% |
| EDTA-Na$_2$ | 0.3% |
| Citric acid to adjust pH to 6.0 | q.s. |
| Preservative | 0.5% |
| Concentrated defensin preparation | 10.0% |
| Purified water | balance |
| Total | 100.0 |

To prepare the face wash formulation all ingredients are mixed together and the volume is brought to about 90 ml. The pH is then adjusted and the volume is finally adjusted to 100 ml (all percentages are weight %). In some embodiments final defensin concentration can range from 1 ng/ml to 10 mg/ml or higher.

The inventors tested a preferred formulation of the inventive subject matter in two clinical studies, Clinical Study 1 and Clinical Study 2 (double-blinded study). Both studies were performed under the supervision of Dr. Gregory Keller, M.D, F.A.C.S at the Plastic Surgery Clinic in Santa Barbara, Calif. The design for both studies was substantially similar. Both clinical studies examined 10 subjects over a duration of 6 weeks. Each subject was given a cream, a serum, and a masque. Half of the subjects (Study 2) were given formulations of the cream, serum, and masques containing defensins. The other half of subjects were given placebo formulations of the cream, serum, and masque that were identical in composition to the test group, except the formulations did not contain defensins.

The inventors measured individual skin health scores for each participant before and after treatment using the QuantifiCare™ 3D LifeViz™ Imaging Clinical System and protocol developed by QuantifiCare Inc. (www.quantificare.com). The faces of each participants were scanned using the 3D LifeViz™ system and given a value for each the following categories: wrinkle depth, length, and width; pore depth; skin evenness; skin oiliness; skin brown spots; and skin red spots. The resulting values for each participant were then compared against a population with the same gender, age, and skin type, using QuantifiCare's Reference Population Database. The resulting skin heath score for each participant was a percentile ranking of skin health when compared with a population of people with the same age, gender, and skin type.

For example, Table 2 (below) shows the average age of each study group when compared to a population with corresponding age, gender, and skin type. Age was calculated using the wrinkle parameter, which is a combination of depth, length, and width of wrinkles in the forehead and cheeks.

TABLE 2

Average Age Ranking For Clinical Study 2 Before and After Treatment

| | Average Age Ranking | |
|---|---|---|
| Group | Before Treatment | After 6 Weeks |
| Placebo | 77% | 74% |
| Test Group | 61% | 81% |

Figure 1B:
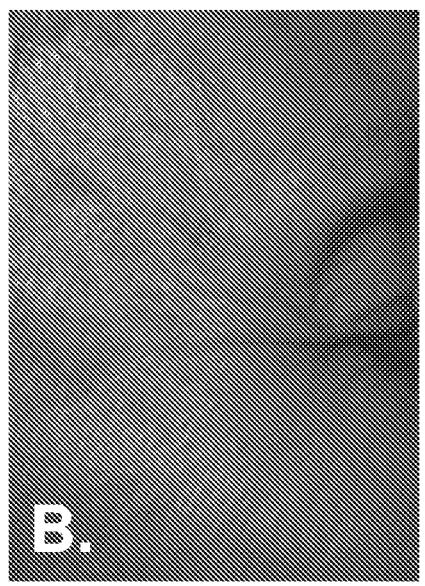

FIGS. 1A and 1B show the before (FIG. 1A) and after (FIG. 1B) images acquired by a 3D LifeViz™ system for participant 3-PC (63 year old female) of Clinical Study 1. Participant 3-PC was given the test formulation. Measurements by the 3D LifeViz™ system showed that participant 3-PC saw a reducing in visible skin age estimation (based on the skin evenness value calculated by the 3D LifeViz™ system) from 64 years to 37 years. Photos have not been retouched.

FIGS. 2A and 2B show before (FIG. 2A) and after (FIG. 2B) images acquired by a 3D LifeViz™ system with the brown-spot filter for participant 8-IK (female) of Clinical Study 1. Participant 3-PC was given the test formulation. Images show a reduction in brown spots on the face as a result of treatment. Photos have not been retouched.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc. Moreover, as used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

What is claimed is:

1. A method of treating melasma in a subject in need thereof, comprising:
   providing a topical formulation comprising a first defensin at a concentration effective to reduce appearance of an extant lesion associated with melasma; and
   topically applying the topical formulation to non-injured skin of the subject in need thereof under a protocol effective to reduce pigmentation of the extant lesion associated with melasma.

2. The method of claim 1, wherein the first defensin is selected from the group consisting of alpha-defensin 1, alpha-defensin 5, alpha-defensin 6, neutrophil defensin 1, neutrophil defensin 2, neutrophil defensin 3, neutrophil defensin 4, theta-defensin, beta-defensin 1, beta-defensin 3, and beta-defensin 4, wherein concentration of the first defensin does not exceed 50 ng/mL.

3. The method of claim 1, wherein the topical formulation further comprises a second defensin, wherein the second defensin is different from the first defensin.

4. The method of claim 1, wherein the topical formulation further comprising a supplement for LGR6+ stem cells, wherein the supplement is selected from the group consisting of human serum albumin, bovine serum albumin, egg albumin, plant hydrolysate, beta-cyclodextrin, glutamine, phospholipids, fibronectin, hyaluronate, plant hydrolysate, L-alanyl-L-glutamine, gelatin, vitamin E, recombinant albumin, hyaluronic acid, epidermal growth factor, fibroblast growth factor, recombinant gelatin, Tocopheryl Nicotinate, Coenzyme Q10, and ubiquinone.

5. A method of reducing appearance of a lesion associated with melasma in non-injured skin of a subject in need thereof comprising:

providing a topical formulation comprising a first defensin at a concentration effective to recruit LGR6+ stem cells to an interfollicular space in non-injured skin; and topically applying the topical formulation to an extant melasma lesion of the subject in need thereof under a protocol effective to reduce pigmentation of the extant lesion associated with melasma.

6. The method of claim 5, wherein the first defensin is selected from the group consisting of alpha-defensin 1, alpha-defensin 5, alpha-defensin 6, neutrophil defensin 1, neutrophil defensin 2, neutrophil defensin 3, neutrophil defensin 4, theta-defensin, beta-defensin 1, beta-defensin 3, and beta-defensin 4, wherein concentration of the first defensin does not exceed 50 ng/mL.

7. The method of claim 5, wherein the topical formulation further comprises a second defensin, wherein the second defensin is different from the first defensin.

8. The method of claim 5, wherein the topical formulation further comprising a supplement for LGR6+ stem cells, wherein the supplement is selected from the group consisting of human serum albumin, bovine serum albumin, egg albumin, plant hydrolysate, beta-cyclodextrin, glutamine, phospholipids, fibronectin, hyaluronate, plant hydrolysate, L-alanyl-L-glutamine, gelatin, vitamin E, recombinant albumin, hyaluronic acid, epidermal growth factor, fibroblast growth factor, recombinant gelatin, Tocopheryl Nicotinate, Coenzyme Q10, and ubiquinone.

9. The method of claim 5, wherein melasma is epidermal melasma.

* * * * *